US010617851B2

(12) United States Patent
Jalgaonkar et al.

(10) Patent No.: US 10,617,851 B2
(45) Date of Patent: Apr. 14, 2020

(54) MEDICAL CATHETER SYSTEM

(71) Applicant: Covidien LP, Mansfield, MA (US)

(72) Inventors: Ujwal Jalgaonkar, Irvine, CA (US); Edwin Wang, Tustin, CA (US); Edwin Bon, Lake Elsinore, CA (US)

(73) Assignee: Covidien LP, Mansfield, MA (US)

( * ) Notice: Subject to any disclaimer, the term of this patent is extended or adjusted under 35 U.S.C. 154(b) by 841 days.

(21) Appl. No.: 15/086,151

(22) Filed: Mar. 31, 2016

(65) Prior Publication Data

US 2017/0281915 A1    Oct. 5, 2017

(51) Int. Cl.
*A61M 25/10* (2013.01)
*A61M 25/00* (2006.01)

(52) U.S. Cl.
CPC .... *A61M 25/1011* (2013.01); *A61M 25/0023* (2013.01); *A61M 25/0043* (2013.01); *A61M 25/003* (2013.01); *A61M 25/0032* (2013.01); *A61M 2025/1015* (2013.01); *A61M 2025/1052* (2013.01); *A61M 2205/32* (2013.01)

(58) Field of Classification Search
CPC ...... A61M 25/1011; A61M 2025/1013; A61M 25/0023; A61M 25/0042; A61M 2025/1015
See application file for complete search history.

(56) References Cited

U.S. PATENT DOCUMENTS

| | | |
|---|---|---|
| 4,404,971 A | 9/1983 | LeVeen et al. |
| 4,781,677 A * | 11/1988 | Wilcox ................ A61B 17/22 |
| | | 600/561 |
| 5,163,905 A * | 11/1992 | Don Michael ..... A61M 25/1011 |
| | | 604/101.03 |
| 5,578,071 A | 11/1996 | Parodi |
| 5,580,568 A | 12/1996 | Greff et al. |
| 5,667,767 A | 9/1997 | Greff et al. |
| 5,695,480 A | 12/1997 | Evans et al. |
| 5,728,068 A | 3/1998 | Leone et al. |
| 6,096,021 A | 8/2000 | Helm et al. |

(Continued)

FOREIGN PATENT DOCUMENTS

DE    3227575 A1    2/1984

OTHER PUBLICATIONS

Arat et al., "Double-Balloon Remodeling of Wide-Necked Aneurysms Distal to the Circle of Willis," American Journal of Neuroradiology, Aug. 2005, 4 pp.

*Primary Examiner* — Nathan R Price
*Assistant Examiner* — Courtney B Fredrickson
(74) *Attorney, Agent, or Firm* — Shumaker & Sieffert P.A.

(57) ABSTRACT

In some examples, a catheter may include a catheter body, a first expandable member, and a second expandable member. The catheter body may define a first lumen, a second lumen, a delivery port, and a surface extending from the delivery port into the first lumen. The first lumen may define a first central longitudinal axis. The second lumen may define a second central longitudinal axis spaced from the first central longitudinal axis in a direction orthogonal to the second central longitudinal axis. The delivery port may be in fluid communication with the first lumen. The surface extending from the delivery port into the first surface may be oriented at an obtuse or acute angle relative to the first central longitudinal axis.

25 Claims, 9 Drawing Sheets

(56) References Cited

U.S. PATENT DOCUMENTS

| | | | |
|---|---|---|---|
| 6,231,543 B1* | 5/2001 | Hegde | A61M 25/10 |
| | | | 604/96.01 |
| 6,527,790 B2* | 3/2003 | Chien | A61B 17/12022 |
| | | | 606/194 |
| 6,638,243 B2 | 10/2003 | Kupiecki | |
| 7,077,836 B2 | 7/2006 | Lary et al. | |
| 7,645,259 B2 | 1/2010 | Goldman | |
| 7,662,143 B2* | 2/2010 | Carrison | A61M 25/1011 |
| | | | 604/509 |
| 8,162,879 B2 | 4/2012 | Hattangadi et al. | |
| 2004/0039331 A1* | 2/2004 | Coppi | A61B 17/12045 |
| | | | 604/101.04 |
| 2005/0177103 A1 | 8/2005 | Hunter et al. | |
| 2007/0208302 A1* | 9/2007 | Webster | A61M 25/0041 |
| | | | 604/103.04 |
| 2012/0116352 A1 | 5/2012 | Rangi | |
| 2012/0253278 A1 | 10/2012 | Ise | |
| 2014/0214071 A1* | 7/2014 | Thomas | A61B 17/12036 |
| | | | 606/200 |

* cited by examiner

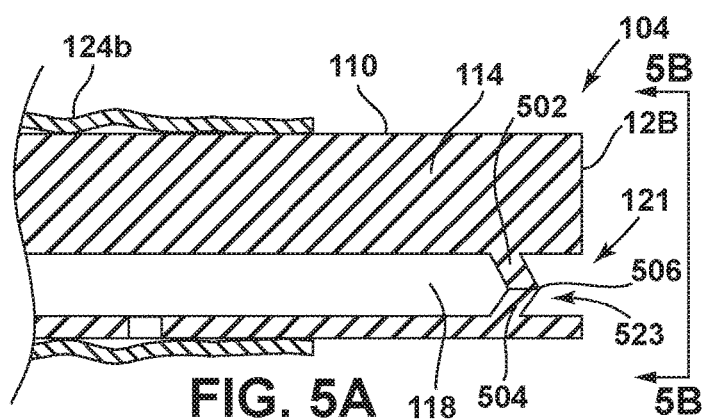
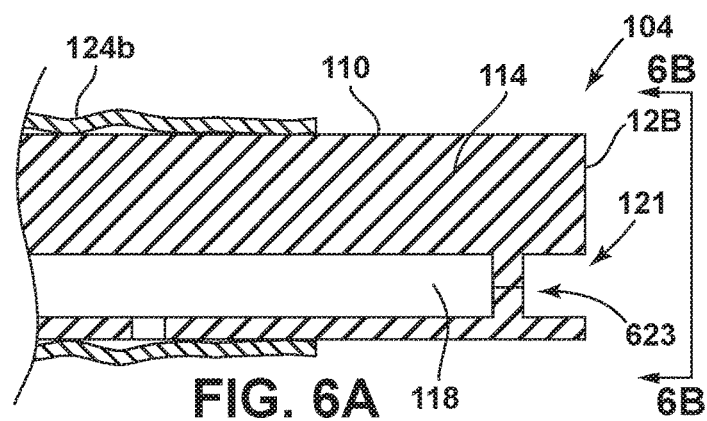
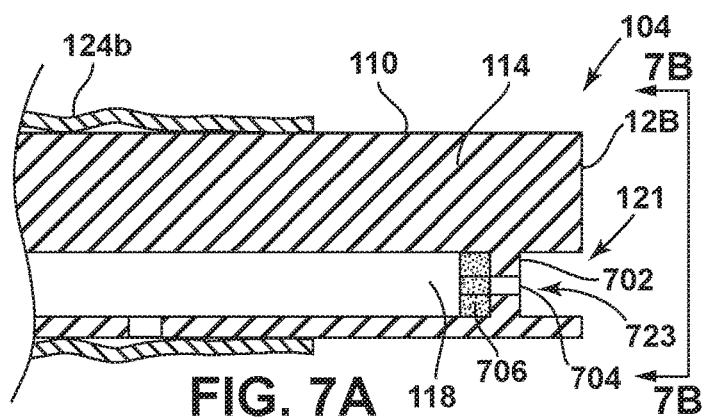

MEDICAL CATHETER SYSTEM

TECHNICAL FIELD

This disclosure relates to a medical catheter system.

BACKGROUND

A medical catheter defining at least one lumen has been proposed for use with various medical procedures. For example, in some cases, a medical catheter may be used to deliver embolic composition to or within an embolization site in a blood vessel of a patient and/or to deliver another agent or device within a vasculature of a patient. In some cases, a medical catheter may be used to access and treat defects in blood vessels, such as, but not limited to, lesions or occlusions in blood vessels.

SUMMARY

In some aspects, this disclosure describes example multi-lumen catheters that each includes a lumen with a delivery port and a surface extending from the delivery port and into the lumen to facilitate delivery of devices and/or agents through the delivery port and to a target tissue site in a patient. For example, a catheter may include a catheter body and two expandable members. The catheter body may define first and second lumens, a delivery port, and a surface extending from the delivery port into the first lumen. The surface extending from the delivery port into the first lumen may be oriented at an obtuse or acute angle relative to a first central longitudinal axis of the first lumen. A first of the two expandable members may be coupled to the catheter body proximal to the delivery port and a second of the expandable members may be coupled to the catheter body distal to the delivery port. The first and second expandable members may be in fluid communication with the second lumen, e.g., which may be configured to deliver an inflation fluid to the expandable members to cause the expandable members to expand radially outwardly from the catheter body.

In some examples, the first lumen of the catheter may be configured to receive a second catheter (e.g., an "inner catheter"), and the surface may form a ramp configured to guide a distal portion of the second catheter from the first lumen through the delivery port. For example, the second catheter may be used to deliver a therapeutic agent or a medical device to tissue of a patient proximate the delivery port. In addition, in some examples, the second lumen may be configured to receive a guide member (e.g., a guidewire or a guide catheter).

Clause 1: In some examples, a catheter comprises a catheter body, a first expandable member, and a second expandable member. The catheter body defines a first lumen defining a first central longitudinal axis; a second lumen defining a second central longitudinal axis spaced from the first central longitudinal axis in a direction orthogonal to the second central longitudinal axis; a delivery port in fluid communication with the first lumen; and a surface extending from the delivery port into the first lumen, wherein the surface is oriented at an obtuse or acute angle relative to the first central longitudinal axis. The first expandable member is coupled to the catheter body proximal to the delivery port and is in fluid communication with the second lumen. The second expandable member is coupled to the catheter body distal to the delivery port and is in fluid communication with the second lumen.

Clause 2: In some examples of the catheter of clause 1, the first and second central longitudinal axes are substantially parallel.

Clause 3: In some examples of the catheter of any of the preceding clauses, the catheter body defines a distal opening, the second lumen terminating at the distal opening.

Clause 4: In some examples of the catheter of any of the proceeding clauses, the second lumen extends distal to the first lumen.

Clause 5: In some examples of the catheter of any of the preceding clauses, the first lumen terminates at the surface.

Clause 6: In some examples of the catheter of any of the preceding clauses, the catheter body comprises a septum defining at least a portion of the first and second lumens, wherein the surface extends from the delivery port to the septum, the septum and the surface defining an obtuse angle.

Clause 7: In some examples of the catheter of any of clauses 1-5, the catheter body comprises a first exterior wall and an interior wall defining the first lumen, and the surface extends from a distal edge of the delivery port to the interior wall, the interior wall and the surface defining an obtuse angle.

Clause 8: In some examples of the catheter of any of the preceding clauses, the surface comprises a radiopaque material.

Clause 9: In some examples of the catheter of any of the preceding clauses, the catheter body comprises a distal member positioned distal to the first lumen, the distal member defining the surface.

Clause 10: In some examples of the catheter of clause 9, the distal member and the second lumen are at least partially coextensive.

Clause 11: In some examples of the catheter of any of the preceding clauses, the first lumen has a first cross-sectional area, and the second lumen has a second cross-sectional area, the cross-sections being taken in a direction substantially orthogonal to one of the first or second central longitudinal axes, and the first and second cross-sectional areas being substantially equal.

Clause 12: In some examples of the catheter of any of clauses 1-10, the first lumen has a first cross-sectional area, and the second lumen has a second cross-sectional area, the cross-sections being taken in a direction substantially orthogonal to one of the first or second central longitudinal axes, and the first and second cross-sectional areas being different.

Clause 13: In some examples of the catheter of any of the preceding clauses, the first expandable member comprises a first inflatable balloon, and the second expandable member comprises a second inflatable balloon.

Clause 14: In some examples of the catheter of clause 0, the balloons are bonded to the catheter body by at least one of an adhesive, heat bonding, or laser bonding.

Clause 15: In some examples of any of the preceding clauses, the first expandable member, when expanded, defines a first dimension measured in a direction substantially orthogonal to the second central longitudinal axis, and the second expandable member, when expanded, defines a second dimension measured in the direction substantially orthogonal to the second central longitudinal, the first and second dimensions being different.

Clause 16: In some examples of the catheter of any of the preceding clauses, the first expandable member, when expanded, defines a first dimension measured in a direction substantially orthogonal to the second central longitudinal axis, and the second expandable member, when expanded, defines a second dimension measured in the direction substantially orthogonal to the second central longitudinal, the first and second dimensions being substantially equal.

Clause 17: In some examples of the catheter of any of clauses 1-16, the first expandable member has a different compliancy than the second expandable member.

Clause 18: In some examples of the catheter of any of the preceding clauses, a distal end of the first expandable member is longitudinally spaced from a proximal end of the second expandable member by about 10 millimeters to about 50 millimeters.

Clause 19: In some examples of the catheter of any of the preceding clauses, the catheter further comprises at least one radiopaque marker adjacent to the delivery port.

Clause 20: In some examples of the catheter of any of the preceding clauses, the catheter further comprises a first radiopaque marker proximal to the delivery port; and a second radiopaque marker distal to the delivery port.

Clause 21: In some examples of the catheter of clause 15, the first radiopaque marker is longitudinally aligned with the first expandable member, and the second radiopaque marker is longitudinally aligned with the second expandable member.

Clause 22: In some examples, a system comprises a first catheter and a second catheter. The first catheter comprises a catheter body, a first expandable member, and a second expandable member. The catheter body defines a first lumen defining a first central longitudinal axis; a second lumen defining a second central longitudinal axis spaced from the first central longitudinal axis in a direction orthogonal to the second central longitudinal axis; a delivery port in fluid communication with the first lumen; and a ramp extending from the delivery port into the first lumen, wherein the ramp is oriented at an obtuse or acute angle relative to the first central longitudinal axis. The first expandable member is coupled to the catheter body proximal to the delivery port and is in fluid communication with the second lumen. The second expandable member is coupled to the catheter body distal to the delivery port and is in fluid communication with the second lumen. The second catheter is configured to be received within the first lumen. The ramp is configured to guide a distal portion of the second catheter from the first lumen through the delivery port.

Clause 23: In some examples of the system of clause 0, the second catheter is configured to deliver a therapeutic agent to tissue of a patient.

Clause 24: In some examples of the system of any of clauses 22-23, the second catheter is configured to deliver a medical device to a target tissue site.

Clause 25: In some examples of the system of any of clauses 22-24, the system further comprises a guidewire, wherein the second lumen is configured to receive the guidewire.

Clause 26: In some examples of the system of any of clauses 22-25, the first and second central longitudinal axes are substantially parallel.

Clause 27: In some examples of the system of any of clauses 22-26, the catheter body defines a distal opening, the second lumen terminating at the distal opening.

Clause 28: In some examples of the system of any of clauses 22-27, the second lumen extends distal to the first lumen.

Clause 29: In some examples of the system of any of clauses 22-28, the first lumen terminates at the surface.

Clause 30: In some examples of the system of any of clauses 22-29, the catheter body comprises a septum separating the first and second lumens, wherein the surface extends from the delivery port to the septum, the septum and the surface defining an obtuse angle.

Clause 31: In some examples of the system of any of clauses 22-29, the catheter body comprises a first exterior wall and an interior wall defining the first lumen, and the surface extends from a distal edge of the delivery port to the interior wall, the interior wall and the surface defining an obtuse angle Clause 32: In some examples of the system of any of clauses 22-31, the surface comprises a radiopaque material.

Clause 33: In some examples of the system of any of clauses 22-32, the catheter body comprises a distal member positioned distal to the first lumen, the distal member defining the surface.

Clause 34: In some examples of the system of clause 33, the distal member and the second lumen are at least partially coextensive.

Clause 35: In some examples, a method of forming a catheter comprises coupling a first expandable member to a catheter body proximal to a delivery port defined by the catheter body; and coupling a second expandable member to the catheter body distal to the delivery port. The catheter body further defines a first lumen defining a first central longitudinal axis; a second lumen defining a second central longitudinal axis spaced from the first central longitudinal axis in a direction orthogonal to the second central longitudinal axis, the delivery port being in fluid communication with the first lumen; and a surface extending from the delivery port into the first lumen, wherein the surface is oriented at an obtuse or acute angle relative to the first central longitudinal axis. Coupling the first and second expandable members to the catheter body comprises fluidically connecting the first and second expandable members to the second lumen.

Clause 36: In some examples of the method of clause 35, coupling the first expandable member and the second expandable member to the catheter body comprises adhesive bonding at least a portion of the first expandable member and at least a portion of the second expandable member to the catheter body.

Clause 37: In some examples of the method of clause 35, coupling the first expandable member and the second expandable member to the catheter body comprises heat bonding at least a portion of the first expandable member and at least a portion of the second expandable member to the catheter body.

Clause 38: In some examples of the method of clause 35, coupling the first expandable member and the second expandable member to the catheter body comprises laser bonding at least a portion of the first expandable member and at least a portion of the second expandable member to the catheter body.

Clause 39: In some examples of the method of any of clauses 35-38, the catheter body comprises a first wall and a second wall defining the first lumen and the method further comprises defining the surface, wherein defining the surface comprises coupling a distal member to the second wall distal to the first lumen, the distal member defining the surface.

Clause 40: In some examples of the method of any of clauses 35-39, the first and second central longitudinal axes are substantially parallel.

Clause 41: In some examples of the method of any of clauses 35-40, the catheter body defines a distal opening, the second lumen terminating at the distal opening.

Clause 42: In some examples of the method of any of clauses 35-41, the second lumen extends distal to the first lumen.

Clause 43: In some examples of the method of any of clauses 35-42, the first lumen terminates at the surface.

Clause 44: In some examples of the method of any of clauses 35-43, the catheter body comprises a septum separating the first and second lumens and the surface extends from the delivery port to the septum, the septum and the surface defining an obtuse angle.

Clause 45: In some examples of the method of any of clauses 35-43, the catheter body comprises a first exterior wall and an interior wall defining the first lumen, and the surface extends from a distal edge of the delivery port to the interior wall, the interior wall and the surface defining an obtuse angle Clause 46: In some examples of the method of any of clauses 35-45, the surface comprises a radiopaque material.

Clause 47: In some examples of the method of any of clauses 35-46, the catheter body comprises a distal member positioned distal to the first lumen, the distal member defining the surface.

Clause 48: In some examples of the method of any of clauses 35-47, the distal member and the second lumen are at least partially coextensive.

Clause 49: In some examples of the method of any of clauses 35-48, the first lumen has a first cross-sectional area, and the second lumen has a second cross-sectional area, the cross-sections being taken in a direction substantially orthogonal to one of the first or second central longitudinal axes, and the first and second cross-sectional areas being substantially equal.

Clause 50: In some examples of the method of any of clauses 35-48, the first lumen has a first cross-sectional area, and the second lumen has a second cross-sectional area, the cross-sections being taken in a direction substantially orthogonal to one of the first or second central longitudinal axes, and the first and second cross-sectional areas being different.

Clause 51: In some examples of the method of any of clauses 35-50, the first expandable member comprises a first inflatable balloon, and the second expandable member comprises a second inflatable balloon.

Clause 52: In some examples of the method of clause 51, coupling the first expandable member and the second expandable member to the catheter body comprises bonding the balloons to the catheter body by at least one of an adhesive, heat bonding, or laser bonding.

Clause 53: In some examples of the method of any of clauses 35-52, the first expandable member, when expanded, defines a first dimension measured in a direction substantially orthogonal to the second central longitudinal axis, and the second expandable member, when expanded, defines a second dimension measured in the direction substantially orthogonal to the second central longitudinal, the first and second dimensions being different.

Clause 54: In some examples of the method of any of clauses 35-53, the first expandable member, when expanded, defines a first dimension measured in a direction substantially orthogonal to the second central longitudinal axis, and the second expandable member, when expanded, defines a second dimension measured in the direction substantially orthogonal to the second central longitudinal, the first and second dimensions being substantially equal.

Clause 55: In some examples of the method of any of clauses 35-54, the first expandable member has a different compliancy than the second expandable member.

Clause 56: In some examples of the method of any of clauses 35-55, coupling the first and second expandable members to the catheter body comprises coupling the first and second expandable members to the catheter body such that a distal end of the first expandable member is longitudinally spaced from a proximal end of the second expandable member by about 10 millimeters to about 50 millimeters.

Clause 57: In some examples of the method of any of clauses 35-56, the method further comprises applying at least one radiopaque marker adjacent to the delivery port.

Clause 58: In some examples of the method of any of clauses 35-57, the method further comprises applying a first radiopaque marker proximal to the delivery port; and applying a second radiopaque marker distal to the delivery port.

Clause 59: In some examples of the method of clause 58, the method further comprises applying the first radiopaque marker such that it is longitudinally aligned with the first expandable member; and applying the second radiopaque marker such that it is longitudinally aligned with the second expandable member.

Clause 60: In some examples, a method comprises inserting a guide member into a vasculature of a patient; introducing a catheter over the guide member. The catheter comprises a catheter body, a first expandable member and a second expandable member. The catheter body defines a first lumen defining a first central longitudinal axis; a second lumen defining a second central longitudinal axis spaced from the first central longitudinal axis in a direction orthogonal to the second central longitudinal axis; a delivery port in fluid communication with the first lumen; and a surface extending from the delivery port into the first lumen, wherein the surface is oriented at an obtuse or acute angle relative to the first central longitudinal axis. The first expandable member is coupled to the catheter body proximal to the delivery port and in fluid communication with the second lumen. The second expandable member is coupled to the catheter body distal to the delivery port and in fluid communication with the second lumen. The method further comprises advancing a distal end of the catheter body to a treatment site; inflating the first expandable member; inflating the second expandable member; and delivering a therapeutic agent or a medical device through the delivery port.

Clause 61: In some examples of the method of clause 60, the method comprises delivering the medical device through the delivery port, the medical device comprising a coil member.

Clause 62: In some examples of the method of any of clauses 60-61, the method comprises delivering the therapeutic agent through the delivery port, the therapeutic agent comprising an embolic agent.

Clause 63: In some examples of the method of any of clauses 60-62, the first and second central longitudinal axes are substantially parallel.

Clause 64: In some examples of the method of any of clauses 60-63, the catheter body defines a distal opening, the second lumen terminating at the distal opening.

Clause 65: In some examples of the method of any of clauses 60-64, the second lumen extends distal to the first lumen.

Clause 66: In some examples of the method of any of clauses 60-65, the first lumen terminates at the surface.

Clause 67: In some examples of the method of any of clauses 60-66, the catheter body comprises a septum separating the first and second lumens and the surface extends from the delivery port to the septum, the septum and the surface defining an obtuse angle.

Clause 68: In some examples of the method of any of clauses 60-66, the catheter body comprises a first exterior wall and an interior wall defining the first lumen, and the surface extends from a distal edge of the delivery port to the interior wall, the interior wall and the surface defining an obtuse angle Clause 69: In some examples of the method of any of clauses 60-68, the surface comprises a radiopaque material.

Clause 70: In some examples of the method of any of clauses 60-69, the catheter body comprises a distal member positioned distal to the first lumen, the distal member defining the surface.

Clause 71: In some examples of the method of any of clause 70, the distal member and the second lumen are at least partially coextensive.

Clause 72: In some examples of the method of any of clauses 60-71, the first lumen has a first cross-sectional area, and the second lumen has a second cross-sectional area, the cross-sections being taken in a direction substantially orthogonal to one of the first or second central longitudinal axes, and the first and second cross-sectional areas being substantially equal.

Clause 73: In some examples of the method of any of the clauses 60-71, the first lumen has a first cross-sectional area, and the second lumen has a second cross-sectional area, the cross-sections being taken in a direction substantially orthogonal to one of the first or second central longitudinal axes, and the first and second cross-sectional areas being different.

Clause 74: In some examples of the method of any of clauses 60-73, the first expandable member comprises a first inflatable balloon, and the second expandable member comprises a second inflatable balloon.

Clause 75: In some examples of the method of any of clause 74, the balloons are bonded to the catheter body by at least one of an adhesive, heat bonding, or laser bonding.

Clause 76: In some examples of the method of any of clauses 60-75, the first expandable member, when expanded, defines a first dimension measured in a direction substantially orthogonal to the second central longitudinal axis and the second expandable member, when expanded, defines a second dimension measured in the direction substantially orthogonal to the second central longitudinal, the first and second dimensions being different.

Clause 77: In some examples of the method of any of clauses 60-75, the first expandable member, when expanded, defines a first dimension measured in a direction substantially orthogonal to the second central longitudinal axis and the second expandable member, when expanded, defines a second dimension measured in the direction substantially orthogonal to the second central longitudinal, the first and second dimensions being substantially equal.

Clause 78: In some examples of the method of any of clauses 60-77, the first expandable member has a different compliancy than the second expandable member.

Clause 79: In some examples of the method of any of clauses 60-78, a distal end of the first expandable member is longitudinally spaced from a proximal end of the second expandable member by about 10 millimeters to about 50 millimeters.

Clause 80: In some examples of the method of any of clauses 60-79, the catheter body further comprises at least one radiopaque marker adjacent to the delivery port.

Clause 81: In some examples of the method of any of clauses 60-80, the catheter body further comprises a first radiopaque marker proximal to the delivery port; and a second radiopaque marker distal to the delivery port.

Clause 82: In some examples of the method of clause 81, the first radiopaque marker is longitudinally aligned with the first expandable member, and the second radiopaque marker is longitudinally aligned with the second expandable member.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIGS. 5A-7B are cross-sectional views illustrating examples of valves that the catheter body of the outer catheter of FIGS. 1 and 2 may include in some examples.

DETAILED DESCRIPTION

Figure 1:
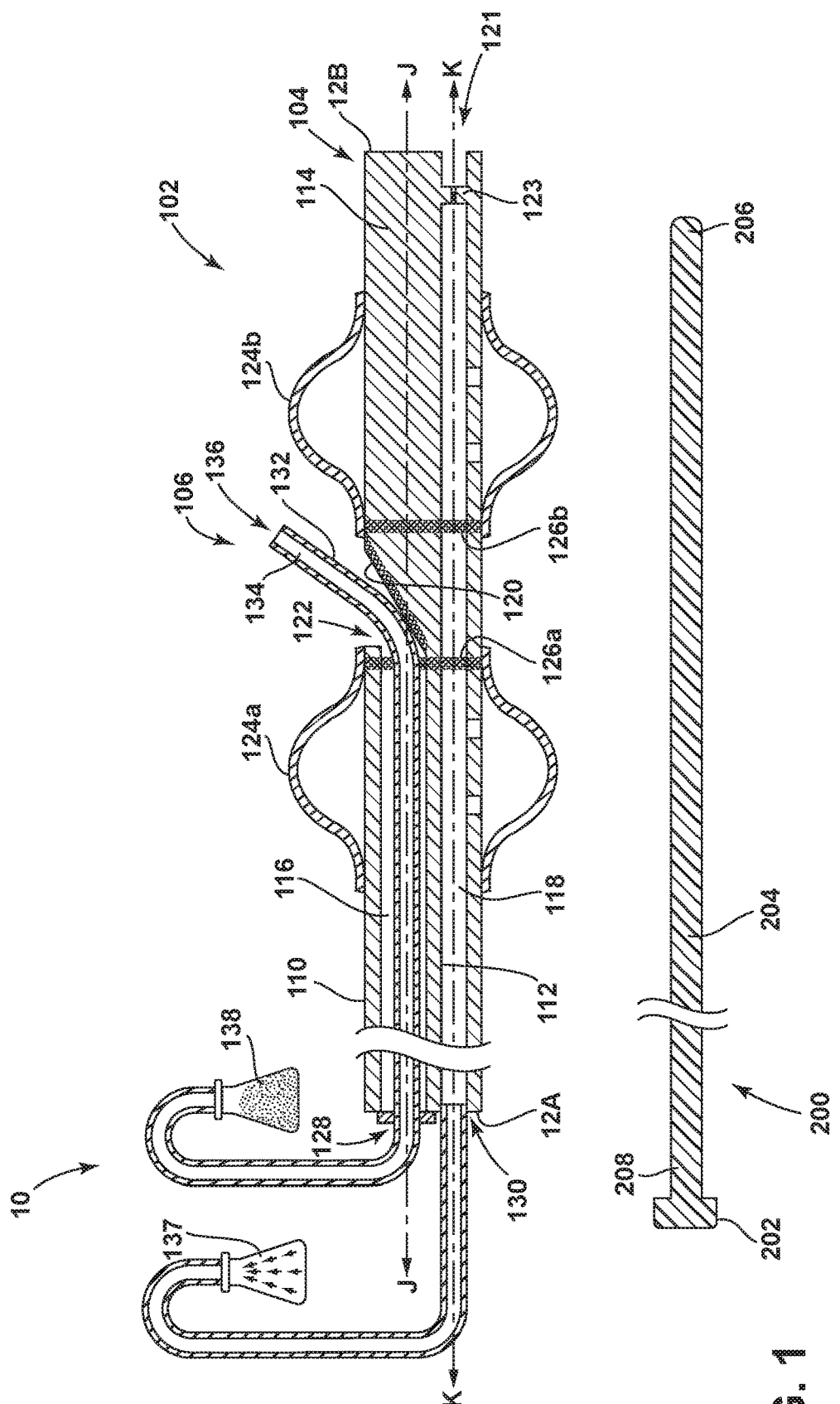
FIG. 1 is a conceptual cross-sectional view of an example system, which includes a multi-lumen outer catheter in fluid communication with a source of inflation fluid, an inner catheter received within a lumen of the outer catheter, and a guidewire.

In some examples, a medical catheter ("catheter") described herein includes a catheter body with a delivery port and an angled surface extending into a lumen of the catheter body from the delivery port to facilitate delivery of a medical device and/or a therapeutic agent to a target tissue site within the patient adjacent the delivery port. The catheter may include two expandable members, with one expandable member on each side of delivery port, that may expand to isolate the treatment site and secure the catheter and delivery port within a patient's vasculature or other tissue site. The catheter body may define first and second lumens that may be substantially adjacent. The first lumen may be fluidically connected to the delivery port and may be used for delivery of the device or therapeutic agent. In some examples, the second lumen may be configured to receive a guide member, e.g., to aid placement of the catheter within the vasculature, and to receive inflation fluid for inflation of the expandable members. For example, the second lumen may include inflation ports for passage of the inflation fluid from the second lumen to the expandable members for inflation of the expandable members.

In some examples, the first lumen of the catheter body may be configured to receive a second catheter (e.g., an "inner catheter") configured to deliver the medical device or the therapeutic agent, and the surface extending from the delivery port into the first lumen may be configured to guide a distal portion, including a distal opening, of the inner catheter toward the target tissue site for delivery of the device or therapeutic agent. A ramp formed by the angled surface that extends from the first lumen of the catheter to the delivery port of the catheter may facilitate guidance of the second catheter for delivery of a therapeutic agent and/or treatment device (e.g., therapeutic agents, medical devices, and the like) and may facilitate more accurate delivery of the therapeutic agent and/or device.

In some examples, the catheter may include one or more radiopaque markers, which may be included on the angled surface, on the catheter body proximate to one or both of the expandable members, on either or both sides of the delivery port, or in any suitable place, to assist with visualization and placement of the catheter, including the delivery port, surface, and expandable members, with respect to the target tissue site.

A catheter with expandable members on either side of a delivery port may allow for isolation of a treatment site, e.g., from blood flow, and may help secure the catheter within vasculature (or another target tissue site) and relative to the treatment site to allow for more precise delivery of therapeutic agents and/or devices. Thus, in some examples, the expandable members of a catheter may help isolate an embolic or other agent to the treatment site, and/or help isolate the treatment site from blood that may interfere with delivery of a device or therapeutic agent.

In some examples, the catheters described herein may be advanced to a target tissue site (or "target location" or "treatment site") within vasculature of the patient in cooperation with a guide member (e.g., a guidewire, a guide catheter, or the like), which may aid in the navigation (e.g., steering and manipulation) of the catheter through the vasculature. For example, an inner lumen of a catheter body may be configured to receive a guidewire, such that the catheter body may be guided through vasculature over the guidewire.

The catheter of the present disclosure may have particular application in an intracranial or neurovascular procedure. However, the catheter may be used in any interventional, diagnostic, and/or therapeutic procedure including coronary vascular, peripheral vascular, and gastro-intestinal applications in addition to a neurovascular application. The catheter may be a component of an apparatus or system used in conjunction with any of the above applications. As discussed in greater detail herein below, the apparatus or system may include additional components including, e.g., a guidewire or another guide member, an embolic fluid source or any other component necessary to facilitate the performance of the contemplated medical procedure.

In the figures below, the full length of the catheter and/or guidewire is not shown. The length of the catheter and/or guidewire can vary depending on the type of interventional procedure, though the length may range from about 30 centimeters (cm) to about 400 cm in some cases. In some examples, catheters and/or guide wires for coronary, peripheral and neurovascular interventions may range from about 100 cm to about 400 cm, or about 170 cm to about 300 cm.

FIG. 1 is a conceptual cross-sectional view of an example system 10, which includes a multi-lumen outer catheter 102 in fluid communication with a source of inflation fluid 137, an inner catheter 106 received within a first lumen 116 of the outer catheter 102, and a guidewire 200. In the example shown in FIG. 1, system 10 is configured to deliver an embolic composition to a patient, and, thus, inner catheter 106 is shown to be in fluid communication with a source of embolic composition 138. In other examples, however, system 10 may be used to deliver other therapeutic agents or medical devices to a patient (e.g., an embolic coil, embolic protection device, and the like).

Outer catheter 102 may include catheter body 104, expandable member 124a, expandable member 124b, and radiopaque markers 126a and 126b. Catheter body 104 may be a flexible elongated body that extends from proximal end 12A to distal end 12B and may include outer member 110, septum 112, distal member 114, and valve 123. Catheter body 104 may define first lumen 116, second lumen 118 terminating at distal opening 121, proximal access port 128, proximal access port 130, delivery port 122, and surface 120. In some examples, the flexible catheter body 104 is configured to substantially conform to the curvature of the vasculature when introduced in the vasculature of a patient.

Catheter body 104 may include proximal end 12A and distal end 12B. The length of catheter body 104 may be selected to be suitable for accessing a target location within the patient from a vascular access point. The target location may depend on the medical procedure for which catheter system 10 is used. For example, if catheter system 10 is a distal access catheter system used to access vasculature in a brain of a patient from a femoral artery access point at the groin of the patient, catheter body 104 may have a length of about 129 centimeters (cm) to about 135 cm, such as about 132 cm, although other lengths may be used.

Although primarily described as being used to reach relatively distal vasculature sites, the catheter systems described herein, including catheter system 10, may readily be configured to be used with other target tissue sites. For example, the catheters may be used to access tissue sites throughout the coronary and peripheral vasculature, the gastrointestinal tract, the urethra, ureters, Fallopian tubes and other body lumens.

Catheter body 104 and other components of outer catheter 102 are described in further detail with reference to FIG. 2.

Inner catheter 106 may include outer member 132, lumen 134, and distal opening 136. Inner catheter 106 may be configured to be received within first lumen 116 of catheter body 104 through a proximal access port 128 of catheter body 104. Inner catheter 106 may include a distal portion including distal opening 136, and surface 120 of catheter body 104 may form a ramp configured to guide the distal portion of inner catheter 106 from first lumen 116 through delivery port 122. For example, surface 120 may help deflect the distal portion of inner catheter 106 laterally away from catheter 102. Surface 120 may help align distal opening 136 of inner catheter 106 with a target tissue site adjacent to or otherwise proximate to delivery port 122 defined by catheter body 104. In some examples, inner catheter 106 may be configured to deliver a therapeutic agent to tissue of a patient. In addition to, or instead of the therapeutic agent, in some examples, inner catheter 106 may be configured to deliver a medical device to a target tissue site. In these examples, the medical device may be delivered through delivery port 122 without a catheter, and surface 120 may help deflect the medical device laterally towards the target delivery site.

Inner catheter 106 is described in further detail with reference to FIGS. 8 and 9.

Inner catheter 106 may be sized to be received by first lumen 116 of outer catheter 102. Inner catheter 106 may also be sized to receive a medical device (e.g., an embolic protection device, a stent, a thrombectomy device, a delivery system used in combination with any of the foregoing, or any combination thereof), a therapeutic agent, or the like. The outer surface of outer member 132 may be lubricious in some examples in order to facilitate the introduction and passage of at least a portion of inner catheter 106 through first lumen 116 of outer catheter 102. In addition, or instead, the inner surface of outer member 132 defining lumen 134 may be lubricious in some examples in order to facilitate the introduction and passage of a device, a therapeutic agent, delivery system or the like, through lumen 134. For example, the material from which the outer member 132 is formed may be lubricious, or outer member 132 may be formed from two or more materials, where the material that defines the inner surface of outer member 132 may be more or less lubricious than the material that defines an outer surface of outer member 132. In addition to, or instead of, being formed from a lubricious material, in some examples, the outer and/or inner surface of outer member 132 may be coated with a lubricious coating.

Example materials from which the outer member 132 may be formed include, but are not limited to, polytetrafluoroethylene (PTFE), fluoropolymer, perfluoroalkyoxy alkane (PFA), fluorinated ethylene propylene (FEP), polyester block amide (PEBA), plyethylene terephthalate (PET), polyurethane (PU), or any combination thereof. For example, outer member 132 may be formed from a non-etched PTFE, e.g., may consist essentially of a non-etched PTFE.

Guidewire 200 (referring again to FIG. 1) may include an actuator or handle 202 and an elongate body 204 extending from the actuator 202. Elongate body 204 may be dimensioned for insertion within the vasculature or a blood vessel of a subject, and may include a leading end 206 and a trailing end 208. The guidewire 200 may include any commonly used guidewire or catheter. Second lumen 118 of catheter body 104 of outer catheter 102 may be configured to receive elongate body 204. In some examples, distal opening 121 may be configured to allow passage of elongate body 204 and may include valve 123 configured to create a seal around elongate body 204 when elongate body 204 extends through distal opening 121 and to substantially close (e.g., to minimize or prevent leakage of fluids out of second lumen 118 or to minimize or prevent the ingress of fluids into second lumen 118) when elongate body 204 is removed from distal opening 121. Thus, in some examples, valve 123 may be configured to keep second lumen 118 substantially closed both when elongate guidewire member 204 is disposed within distal opening 121 and when elongate guidewire member 204 is not disposed within distal opening 121.

Second lumen 118 may be configured to deliver an inflation fluid to expandable members 124a, 124b (collectively, "expandable members 124") in order to expand expandable members 124 from a first non-expanded state to an expanded state in which expandable members 124 extend further radially outward of catheter body 104. As shown in FIG. 1, in some examples, a source of inflation fluid 137 may be in fluid communication with a proximal access port 130 of catheter body 104, where access port 130 is in fluid communication with second lumen 118. Inflation fluid 137 may include fluids such as air, saline, or contrast and may be selectively transmitted to the second lumen 118 to inflate expandable members 124. Inflation fluid 137 may include, for example, saline and/or contrast.

In examples in which inner catheter 106 is used to deliver an embolic composition to a patient via delivery port 122, a source of embolic composition 138 may be in fluid communication with inner catheter 106. Embolic composition 138 may be any biocompatible composition that solidifies within the body such as a biocompatible polymer dissolved in a biocompatible solvent, e.g., dimethylsulfoxide (DMSO), acetone and the like. Examples of embolic compositions are described in U.S. Pat. Nos. 5,667,767, 5,580, 568 and 5,695,480, the entire disclosure of each being incorporated by reference herein. A source of embolic composition 138 may include a syringe, pump or other mechanism to permit a clinician to selectively cause and/or control the flow of embolic composition 138 to and through inner catheter 106.

In other examples, inner catheter 106 may be in fluid communication with a source of another therapeutic agent. In other examples, inner catheter 106 may be configured for delivery of a medical device including, for example, having a distal portion configured to transport the device and release the device using a tether, retractable sheath, and/or any other suitable mechanism for delivery of a medical device.

Figure 2:
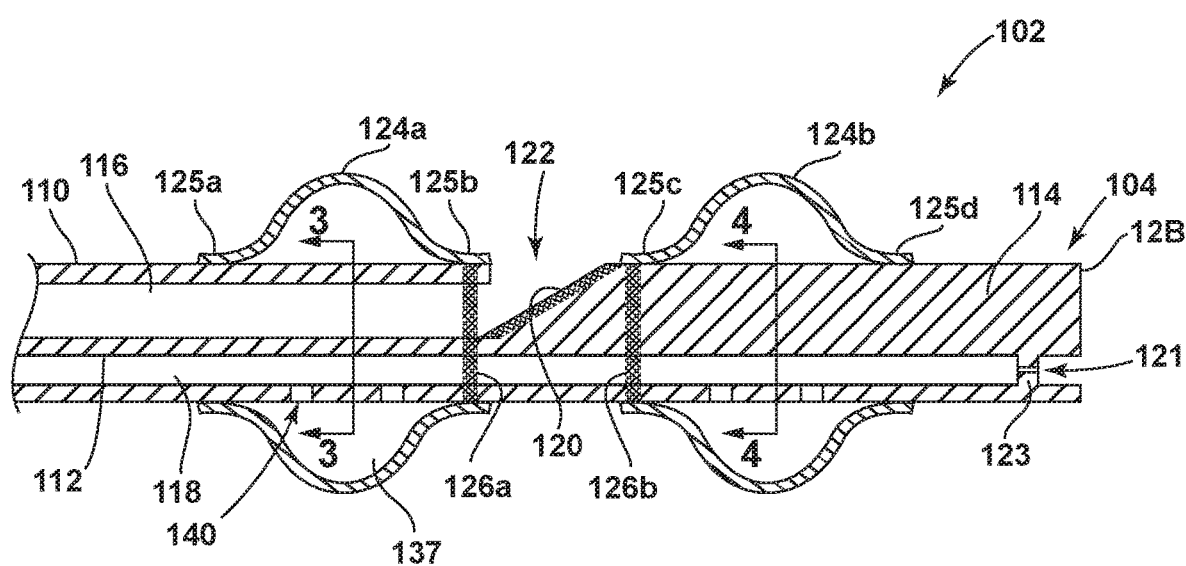
FIG. 2 is a conceptual cross-sectional view of a distal portion of the multi-lumen outer catheter of FIG. 1.

FIG. 2 is a conceptual cross-sectional view of a distal portion of the multi-lumen outer catheter 102 of FIG. 1. Catheter body 104 of outer catheter 102 may include outer member 110, defining an exterior wall of catheter body 104, and septum 112, defining an interior wall and extending within outer member 110 between two substantially adjacent portions of outer member 110, and distal member 114. Septum 112 may separate first lumen 116 and second lumen 118, e.g., together with outer member 110 may define at least a portion of the first lumen 116 and second lumen 118. Distal member 114 may be positioned distal to first lumen 116 and may define surface 120. Distal member 114 may be a structural component that is sized based on the size of first lumen 116 and may be configured to partially or substantially obstruct first lumen 116 and to form an incline with respect to first lumen 116 such that an angled surface 120 of the distal member facing a proximal direction is configured to guide the inner catheter 106 through delivery port 122 and towards a target tissue site.

In some examples, distal member 114 and/or septum 112 may be monolithically formed with outer member 110. In other examples, distal member 144 may be a separate component from outer member 110 and may be attached to outer member 110. For example, a method of forming outer catheter 102 may include coupling distal member 114 to the interior wall defined by septum 112 and/or coupling distal member 114 to the exterior wall defined by outer member 110.

Although distal member 114 is shown as being a solid section of catheter body 104 extending from a point just distal to delivery port 122 to distal end 12B of catheter body 104, distal member 114 may, in some examples, be a member at least partially positioned distal to delivery port 122 to at least partially obstruct lumen 116 but that allows for a hollow portion of catheter body 104 distal to distal member 114. For example, distal member 114 may end before distal end 12B such that the portion of catheter body shown in FIG. 2 as including distal member 114 may define a lumen or otherwise be substantially hollow proximal to distal end 12B, which may improve flexibility of the distal portion of catheter body 104. Instead of or in addition to such configuration(s) of the distal member 114, the distal member may be formed from a material that is more flexible than the material used to form the catheter body 104.

First lumen 116 may define a central longitudinal axis J (shown in FIG. 1). Second lumen 118 may define a central longitudinal axis K (shown in FIG. 1) spaced from central longitudinal axis J in a direction orthogonal to central longitudinal axis K. In certain examples, central longitudinal axes J and K may be substantially parallel (e.g., parallel or nearly parallel). In addition, in certain examples, second lumen 118 may extend distal to first lumen 116. For example, first lumen 116 may terminate at surface 120 and second lumen 118 may terminate at distal opening 121 distal to surface 120.

First lumen 116 may be sized to receive inner catheter 106 and/or another medical device (e.g., an embolic protection device, a stent, a thrombectomy device, a delivery system used in combination with any of the foregoing, or any combination thereof), a therapeutic agent, or the like. The inner surface of outer member 110 and septum 112 defining first lumen 116 may be lubricious in some examples in order to facilitate the introduction and passage of inner catheter 106 and/or any other suitable device, a therapeutic agent, delivery system or the like, through first lumen 116. For example, the material from which the outer member 110 and septum 112 are formed may be lubricious, or outer member 110 and/or septum 112 may be formed from two or more materials, where the material that defines the inner surface of first lumen 116 may be more lubricious than the material that defines an outer surface of outer member 110 or an inner surface defining second lumen 118. In addition to, or instead of, being formed from a lubricious material, in some examples, the inner surface defining first lumen 116 may be coated with a lubricious coating.

Example materials from which the inner surface of first lumen 116 may be formed include, but are not limited to, polytetrafluoroethylene (PTFE), fluoropolymer, perfluoroalkyoxy alkane (PFA), fluorinated ethylene propylene (FEP), polyester block amide (PEBA), plyethylene terephthalate (PET), polyurethane (PU), or any combination thereof. For example, an inner surface of first lumen 116 may be formed from a non-etched PTFE, e.g., may consist essentially of a non-etched PTFE.

Second lumen 118 may be suitably sized to receive and allow passage of elongate body 204 of guidewire 200 (FIG. 1) and to allow passage of inflation fluid 137 through lumen 118 and inflation ports 140 and into expandable members 124. Like the inner surface defining first lumen 116, the inner surface defining lumen 118 may be lubricious in some examples in order to facilitate passage of elongate body 204 and may be formed from, for example, any of the materials described above with reference to first lumen 116.

Delivery port 122 may be an opening defined by outer member 110 and may be in fluid communication with first lumen 116. Delivery port 122 may be configured to allow passage of a distal portion of inner catheter 106 through delivery port 122 or allow passage of another medical device or medical therapeutic agent through delivery port 122 without the use of a delivery catheter. Delivery port 122 may be any suitable size and/or shape according to particular needs.

Surface 120 may be defined, for example by distal member 114 (or by a separate member adjacent to and/or supported by distal member 114) and may extend from delivery port 122 into first lumen 116 and may be oriented at an obtuse or acute angle relative to central longitudinal axis J. In this way, surface 120, which faces proximal end 12A of catheter 12, is not perpendicular to central longitudinal axis J of first lumen 116, but, rather, is oriented at a non-perpendicular angle with respect to central longitudinal axis J of first lumen 116. In certain examples, surface 120 may extend from delivery port 122 (e.g., a distal and/or outer edge of delivery port 122) to septum 112 (e.g., an interior wall of catheter body 104 defined by septum 112). In certain examples, first lumen 116 may terminate at surface 120. In some examples, catheter body 104 may comprise a distal member defining surface 120. For example, although surface 120 is illustrated as being defined by a solid distal member 114 extending from surface 120 to distal end 12B of catheter body 104, distal member 114 may terminate substantially proximal to distal end 12B.

In some examples, surface 120 may comprise a radiopaque material. This may allow for a clinician, for example, to visualize surface 120, including visualizing the proximity of surface 120 to a target tissue site and visualizing the longitudinal, lateral and/or rotational orientation of surface 120 to the target tissue site. For example, a clinician may be able to determine whether surface 120 is positioned adjacent to the target tissue site and to determine whether surface 120 is inclined towards the target tissue site such that surface 120 may be used to guide inner catheter 106 and/or another component or agent though delivery port 122 and towards the target tissue site. The visualization may allow for a clinician to properly position surface 122 with respect to the target tissue site. For example, the clinician may be able to advance and/or retract outer catheter 102 with respect to the target tissue site until the surface 120 is adjacent to the target tissue site and/or may be able to rotate outer catheter 102 within the vasculature until surface 120 is inclined towards the target tissue site.

In some examples, second lumen 118 may be configured to receive a guide member (e.g., guidewire 200), which may facilitate positioning of catheter body 104 within vasculature of a patient. Catheter body 104 may define distal opening 121 at the distal end of second lumen 118 for allowing passage of elongate body 204 of guidewire 200 out of second lumen 118. In some examples, distal opening 121 may include valve 123 for keeping second lumen 118 closed when elongate body 204 is disposed within distal opening 121 and when elongate body 204 is not disposed within distal opening 121, preventing ingress of fluids, including, for example, blood, into second lumen 118 through distal opening 121 and preventing passage of a fluid (e.g., inflation fluid) out of distal opening 121. Preventing ingress of fluids into lumen 118 may help prevent inadvertent obstruction of inflation ports 140 for expandable members 124, which may interfere with the ability to properly expand and deflate expandable members 124. Example configurations of valve 123 are described in further detail below with reference to FIGS. 5A-7B.

Expandable members 124 may each be structures (e.g., inflatable balloons) disposed on either side of delivery port 122 that may be expanded to engage with the walls of the vasculature (or otherwise engage with tissue, which may or may not be within vasculature if catheter 10 is not used within vasculature) to isolate a target tissue site and to secure the position of outer catheter 102 within the vasculature such that the surface 120 and delivery port 122 are securely positioned with respect to the target tissue site. Expandable members 124 are in fluid communication with second lumen 118 by inflation ports 140 and are configured to inflate upon passage of inflation fluid 137 through second lumen 118. When deflated, expandable members 124 may each be in a first state and when inflated, expandable members 124 may each be in a second state in which the members 124 extend further radially outward from catheter body 104 compared to the first state.

Expandable member 124a may be coupled to catheter body 104 proximal to delivery port 122, and expandable member 124b may be coupled to catheter body 104 distal to delivery port 122. In some examples, expandable members 124 may be bonded to catheter body 104, for example, by adhesive, heat bonding, and/or laser bonding. For example, a method of forming outer catheter 102 may include adhesive, heat, and/or laser bonding at least a portion of the expandable member 124a and at least a portion of expandable member 124b to catheter body 104.

When catheter body 104 is placed within a vascular lumen, engagement of the expandable members 124 with vasculature walls (defining the vascular lumen) may help isolate a target tissue site, e.g., by stopping blood flow between the expandable members 124 to allow for delivery of a therapeutic agent and/or a medical device at the target tissue site with less interference from the blood flow through the vasculature. Engagement of the expandable members 124 may also help secure a position of catheter body 104 relative to the target tissue site, which may help secure the position of delivery port 122 and surface 120 in position with respect to the target tissue site, to facilitate delivery of the therapeutic agent and/or a medical device at the target tissue site.

When expanded, expandable members 124 may be substantially different or substantially similar in size. For example, although FIGS. 1 and 2 show expandable members 124 each expanded and having substantially similar diameters, expandable members 124 may also have substantially different diameters when expanded. For example, the diameter of expandable member 124a may be substantially larger than, smaller than, or equal to the diameter of expandable member 124b. Different expanded sizes of expandable members 124 may be useful, for example, for engagement within portions of the vasculature that are different in size. For example, in some examples, the target tissue site may be a bifurcation aneurysm and each of the expandable members 124 may be within a different branch of the vasculature and each branch may be of a different size. In some examples, expandable member 124b may have a smaller diameter than expandable member 124a to accommodate the reduced size of a distal portion of a vasculature to be engaged by expandable member 124b relative to a more proximal portion to be engaged by expandable member 124a.

In some examples, expandable members 124 may have substantially different or similar compliancy. For example, the compliancy of expandable member 124a may be substantially more than, less than, or equal to the compliancy of expandable member 124b. The differences in compliancy may help to result in the different expanded sizes of expandable members 124, as previously described, when inflation fluid is delivered to the members 124 through a common second lumen 118.

Expandable member 124a may include proximal end 125a and distal end 125b and expandable member 124b may include proximal end 125c and distal end 125d. In some examples, distal end 125b of expandable member 124a may be longitudinally spaced from proximal end 125c of expandable member 124b by about 10 millimeters to about 50 millimeters. Expandable members 124 may be spaced from the delivery port 122 and/or from each other by any suitable distance according to particular needs. For example, for a larger target tissue site, it may be desirable to space expandable members 124 further from each other to allow for isolation of the larger target tissue site. In addition, expandable members 124 may be a fixed distance relative to each other or may be movable relative to each other in examples.

In some examples, a clinician may find it desirable to visualize the position of delivery port 122 and/or other components of outer catheter 102. In some examples, catheter body 104 may include one or more radiopaque markers to facilitate visualization of delivery port 122 and/or other components of outer catheter 102. In some examples, at least one radiopaque marker may be adjacent to delivery port 122. For example, as shown in FIG. 2, catheter 102 may include radiopaque marker 126a may be proximal to delivery port 122 and radiopaque marker 126b may be distal to delivery port 122. For example, radiopaque markers 126a and 126b may be longitudinally aligned with expandable members 124a and 124b, respectively. In some examples, catheter body 104 may include additional radiopaque markers. For example, catheter body 104 may include radiopaque markers proximal to expandable member 124a and/or distal to expandable member 124b to facilitate visualizing the outer extents of expandable member 124.

Radiopaque markers 126 may be, for example, a radiopaque marker band (e.g., a ring or one or more partial rings) attached to catheter body 104, e.g., by an adhesive or weld, or held in place between an outer jacket and an inner liner of catheter body 104. In addition to, or instead of a radiopaque marker band, each radiopaque marker 126 may include one or more grooves protruding from an outer surface of catheter body 104 or defined by and recessed within an outer surface of catheter body 104. Grooves may be, for example, a series of tangential arcs along an inner diameter of catheter body 104 and may be formed from a radiopaque material, or may be filled with a radiopaque material in the case of recessed grooves, which may be visible within the patient with the aid of suitable medical imaging equipment. Radiopaque markers 126 may help a clinician determine an orientation and/or location of catheter body 104, including expandable members 124 and delivery port 122, within a patient.

In some examples, at least a portion of an outer surface of outer catheter 102 includes one or more coatings, such as, but not limited to, an anti-thrombogenic coating, which may help reduce the formation of thrombi in vivo, an anti-microbial coating, and/or a lubricating coating. The lubricating coating may be configured to reduce static friction and/kinetic friction between outer catheter 102 and tissue of the patient as outer catheter 102 is advanced through the vasculature. The lubricating coating can be, for example, a hydrophilic coating. In some examples, the entire working length of outer catheter 102 is coated with the hydrophilic coating. In other examples, only a portion of the working length of outer catheter 102 coated with the hydrophilic coating. This may provide a distal length of outer catheter 102 with which the clinician may grip outer catheter 102, e.g., to rotate outer catheter 102 or push outer catheter 102 through vasculature.

In some examples, the portion of catheter body 104 distal to delivery port 122 may be softer (e.g., less stiff) than the portion to delivery port 122. This may allow for easier manipulation of the distal portion of the catheter body 104 through the vasculature.

Figure 3A:
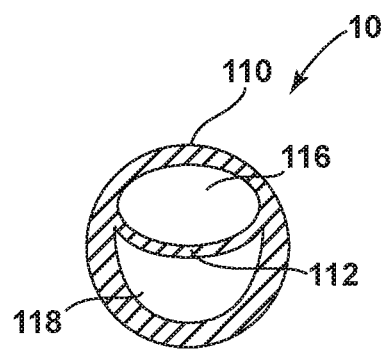
FIGS. 3A-3C are conceptual cross-sectional views of examples of a catheter body of the outer catheter of FIGS. 1 and 2 taken along line 3-3 in FIG. 2.
Figure 3B:
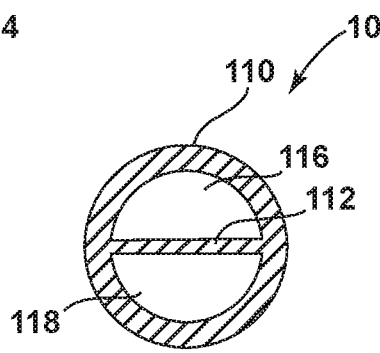
Figure 3C:
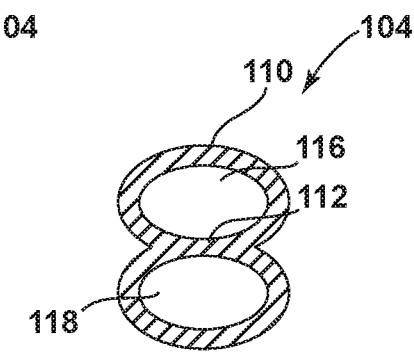

FIGS. 3A-3C are conceptual cross-sectional views of examples of the catheter body 104 of the outer catheter 102 of FIGS. 1 and 2 taken along line 3-3 in FIG. 2. As shown in each of FIGS. 3A-3C and described above with reference to FIGS. 1 and 2, catheter body 104 may include outer member 110 and septum 112 disposed within outer member 110 to define lumens 116 and 118. FIGS. 3A-3C illustrate example configurations, including shapes, of outer member 110, septum 112, first lumen 116, and second lumen 118 and these components may include any suitable configuration and/or shapes according to particular needs. In the example shown in FIG. 3A, a cross-sectional area of first lumen 116 and a cross-sectional area of second lumen 118, are substantially different. In other examples, however, e.g., as shown in FIGS. 3B and 3C, a cross-sectional area of first lumen 116 and a cross-sectional area of 118, may be substantially similar, which may allow for allow for better steerability of the catheter body within vasculature.

Figure 4A:
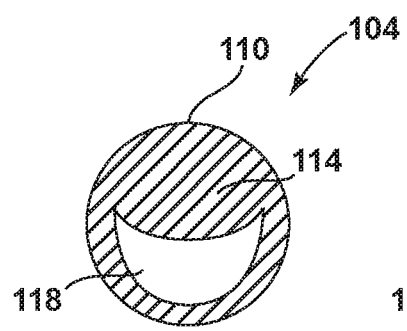
FIGS. 4A-4C are conceptual cross-sectional views of examples of the catheter body of the outer catheter of FIGS. 1 and 2 taken along line 4-4 in FIG. 2.
Figure 4B:
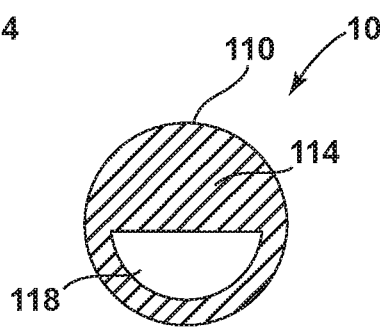
Figure 4C:
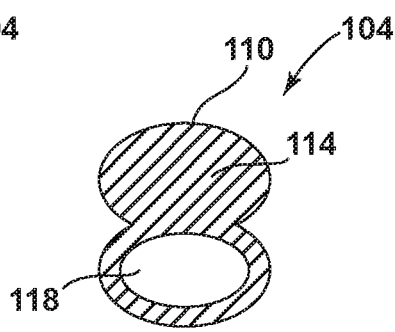

FIGS. 4A-4C are conceptual cross-sectional views of examples of catheter body 104 of the outer catheter 102 of FIGS. 1 and 2 taken along line 4-4 in FIG. 2. As shown in each of FIGS. 4A-4C and described above with reference to FIGS. 1 and 2, catheter body 104 may include outer member 110, distal member 114, and second lumen 118 extending distal to first lumen 116 of FIGS. 3A-3C. In some examples, the catheter body 104 illustrated in each of FIGS. 4A, 4B, and 4C may correspond to the catheter body 104 illustrated in each of FIGS. 3A, 3B, and 3C, respectively. As described above with reference to FIGS. 1 and 2, although distal member 114 is illustrated as being a solid member extending to distal end 12B, distal member 114 may terminate substantially before distal end 12B so that catheter body may include a portion distal to distal member 114 that is substantially hollow (e.g., may include a lumen-like configuration).

In the example illustrated in FIGS. 3A and 4A, outer member 110 may be substantially round and septum 112 may be substantially curved such that the cross-section of first lumen 116 is substantially oval and the cross-sections of second lumen 118 and distal member 114 are substantially crescent shaped. In the example illustrated in FIG. 3B and outer member 110 may be substantially round and septum 112 may be substantially flat such that the cross-sections of first lumen 116, second lumen 118, and distal member 114 are substantially semicircular (e.g., D-shaped). In the example illustrated in FIGS. 3C and 4C, first lumen 116, second lumen 118, and distal member 114 may each be substantially oval and may be defined by any suitable shapes of outer member 110 and septum 112 for defining the oval shapes of first lumen 116, second lumen 118, and distal member 114.

Any suitable shapes and configurations of outer member 110, septum 112, first lumen 116, and second lumen 118 may be used according to particular needs. In some examples, the configuration illustrated in FIGS. 3A and 4A may be preferred to allow for an oval cross-section of first lumen 116 for passage of inner catheter 106, substantially equal cross-sectional areas of first lumen 116 and second lumen 118 for improved steerability, and a round outer member 110 that may allow for the lowest profile of outer member 110 for a first lumen 116 of a particular size. For example, the configurations illustrated in the examples of 3B and 3C may require a larger profile of outer lumen 110 to accommodate a first lumen 116 of equal width while also including a second lumen 118 with a substantially similar cross-sectional area to that of first lumen 116.

FIGS. 5A-7B are cross-sectional views illustrating examples valves, corresponding to valve 123, that the catheter body 104 of the outer catheter 102 of FIGS. 1 and 2 may include in some examples. Each of FIGS. 5A-7B illustrate distal end 12B of catheter body 104 of FIGS. 1 and 2 with expandable member 124b in a deflated configuration and distal opening 121 connected to second lumen 118 by valve 123. Each of FIGS. 5B, 6B, and 7B are conceptual side elevation views of examples of valve 123 of FIGS. 5A, 6A, and 7A, viewed from along lines 5B-5B, 6B-6B, and 7B-7B, respectively. Valve 123 of FIGS. 1 and 2 and the example valves illustrated in each of FIGS. 5A-7B may be configured to allow passage of guidewire 200, to maintain a substantial seal (e.g., a fluid tight seal) around guidewire 200 when guidewire 200 extends through within valve 123 and to substantially close (e.g., to form a fluid tight seal) when guidewire 200 is removed to keep second lumen 118 closed while guidewire 200 extends through valve 123 and when guidewire 200 is not disposed within valve 123. Valve 123 maintaining a substantial seal around guidewire 200 when guidewire 200 extends through valve 123 may help limit or eliminate passage of blood or other fluids into second lumen 118 during placement of outer catheter 102 in a patient's vasculature. Valve 123 substantially closing when guidewire 200 is removed may help limit or eliminate passage of blood or other fluids into second lumen 118 and allow for inflation fluid to be substantially contained within second lumen 118 and expandable members 124 to allow for inflation of expandable members 124 and to limit passage of inflation fluid into the patient's vasculature.

FIGS. 5A and 5B illustrate an example duckbill valve 523 configured generally as a conical or tapered duckbill including first and second leaflets 502 and 504. Leaflets 502 and 504 may be resilient and biased to the closed configuration in which second lumen 118 of the catheter body 104 is completely closed. In some examples, leaflets 502 and 504 may be inclined to depend radially inwardly in the distal direction. The distal incline may allow leaflets 502 and 504 to readily open to permit a sealed passage of guidewire 200 from a proximal direction, and also to resist influx of a fluid such as blood and/or other fluid at a relatively higher pressure into second lumen 118 from the distal side of valve 523. In other examples, a duckbill valve may be provided that exhibits a proximal incline to resist opening when a relatively higher pressure inflation fluid is introduced into inner second lumen 118 to inflate expandable members 124. Leaflets 502 and 504 may be formed monolithically with, or attached to, outer member 110 of catheter body 104. Suitable materials for leaflets 502 and 504 may include thermoplastic elastomers, e.g., polyisoprene, or natural rubber. In an alternative, leaflets 502 and 504 may be fabricated from a low durometer thermoplastic elastomer or a gel material. Other suitable materials may also be used according to particular needs.

FIGS. 6A and 6B illustrate an example tri-leaf valve 623 that may be constructed of a plurality of resilient flaps 602A, 602B, and 602C formed by a plurality of radial slits 604A, 604B, and 604C. Any number of flaps and slits may be provided that cooperate to permit the passage of guidewire 200 and resiliently return to a relatively closed configuration (as illustrated) upon removal of guidewire 200. The flaps 602A, 602B, and 602C may be constructed of a resilient material to provide a bias to return the flaps 602A, 602B, and 602C to the closed configuration in which second lumen 118 is closed. Resilient flaps 602A, 602B, and 602C may be formed monolithically with, or attached to, outer member 110 of catheter body 104. Suitable materials for resilient flaps 602A, 602B, and 602C may include thermoplastic elastomers, e.g., polyisoprene, or natural rubber. As another example, resilient flaps 602A, 602B, and 602C may be fabricated from a low durometer thermoplastic elastomer or a gel material. Other suitable materials may also be used according to particular needs.

FIGS. 7A and 7B illustrate an example valve 723 including a self-sealing or closing plug or membrane 706 positioned proximally with respect to a flexible membrane 702. Flexible membrane 702 may be formed monolithically with, or attached to, outer member 110 of catheter body 104. Membrane 702 may define an aperture 704 that is configured to receive elongate body 204 of guidewire 200. For example, aperture 704 may have a diameter of about 0.125 mm (about 0.005 inches) and membrane 702 may be constructed of a material having sufficient resilience to permit elastic expansion of the aperture 180 to facilitate passage of elongate body 204 of the guidewire 200 there through while also creating a substantial sealing relation about the outer surfaces of elongate body 204.

Suitable materials for the membrane 702 may include thermoplastic elastomers, e.g., polyisoprene, or natural rubber. As other examples, membrane 702 may be fabricated from a low durometer thermoplastic elastomer or a gel material (e.g., an active hydrogel). Other suitable materials may also be used according to particular needs. In examples in which membrane 702 is formed from an active hydrogel (e.g., consisting essentially of a hydrogel), membrane 702 may provide a seal with a guidewire 200 as outer catheter 102 is moved along the guidewire 200 to position outer catheter 102 within a vasculature. Thereafter, the guidewire 200 may be withdrawn through second lumen 118 permitting blood to move through an aperture 704 in the membrane 702 to contact the membrane 706. In the presence of blood, the hydrogel membrane 706 may swell to occupy an entire inner diameter of the second lumen 118.

Figure 8:
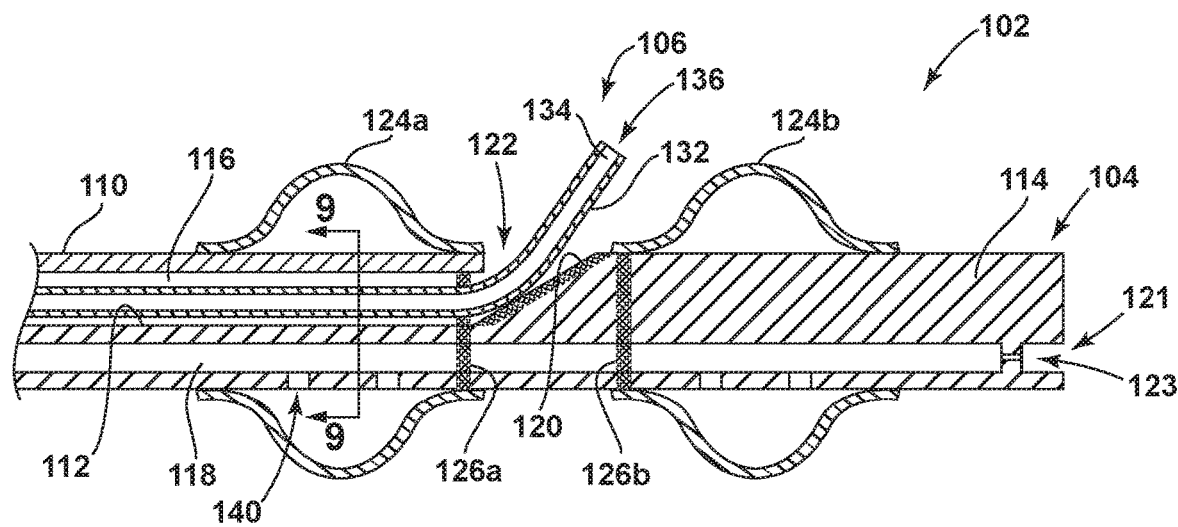
FIG. 8 is a conceptual cross-sectional view of distal portions of the outer catheter and inner catheter of FIG. 1.

FIG. 8 is a conceptual cross-sectional view of distal portions of the outer catheter 102 and inner catheter 106 of FIG. 1. As described above with reference to FIG. 1, first lumen 116 of outer catheter 102 may be configured to receive inner catheter 106. As a distal portion of inner catheter 106 is advanced within first lumen 116 and comes in contact with surface 120, surface 120 may be configured to cause the distal portion of inner catheter 106 to bend away from longitudinal axis J of first lumen 116. As the distal portion of inner catheter 106 is further advanced, it may extend through delivery port 122, guided by surface 120.

Figures 9A, 9B, 9C:
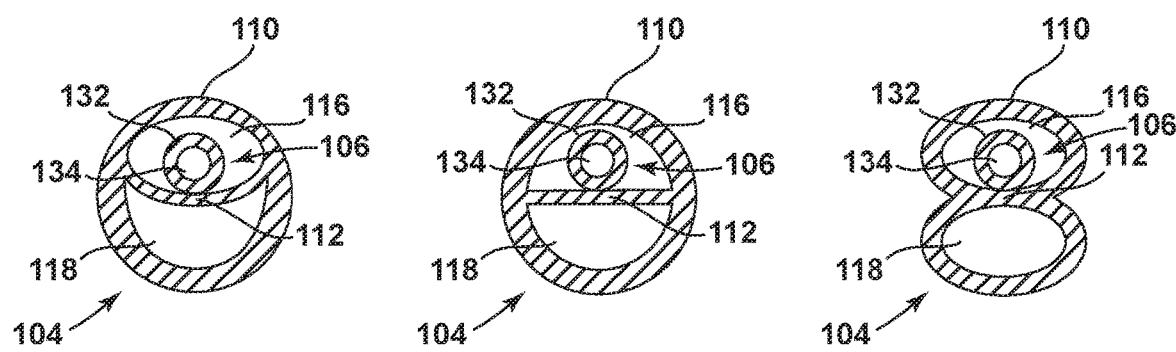
FIGS. 9A-9C are conceptual cross-sectional views of examples of the catheter body, of the outer catheter, and the inner catheter of FIG. 1 taken along line 9-9 in FIG. 8.

FIGS. 9A-9C are conceptual cross-sectional views of examples of the catheter body 104, of the outer catheter 102, and the inner catheter 106 of FIG. 1 taken along line 9-9 in FIG. 8. As described above with reference to FIGS. 3A-3C, catheter body 104 may include any suitable configuration of outer member 110, septum 112, first lumen 116, and second lumen 118. First lumen 116 may be configured to receive inner catheter 106 for passage of inner catheter 106 through first lumen 116. Although illustrated as being substantially round, inner catheter 106 may be any suitable shape according to particular needs. Additionally, inner catheter 106 may fill more or less space within first lumen 116.

FIGS. 10A-10G are partial, schematic views of the system of FIG. 1 in various stages of use at a treatment site adjacent to an example target location 1002 of a vasculature 1000 of a patient. Vasculature 1000 may include walls that define vascular lumen 1004 and target location 1002 may be a treatment site within vasculature 1000. Target location 1002 may be, for example, an aneurysm. In other examples, a treatment site that catheter 102 may be used to reach may be a vascular structure other than an aneurysm, for example an arteriovenous malformation, arteriovenous fistula, or branch vessel, or outside of vasculature, e.g., within another body lumen or another tissue site within a patient. The target location 1002 may alternatively be a device or implant, e.g. a device or implant in need of augmentation, repair, further assembly, alteration, expansion, contraction, etc.

Figure 10A:
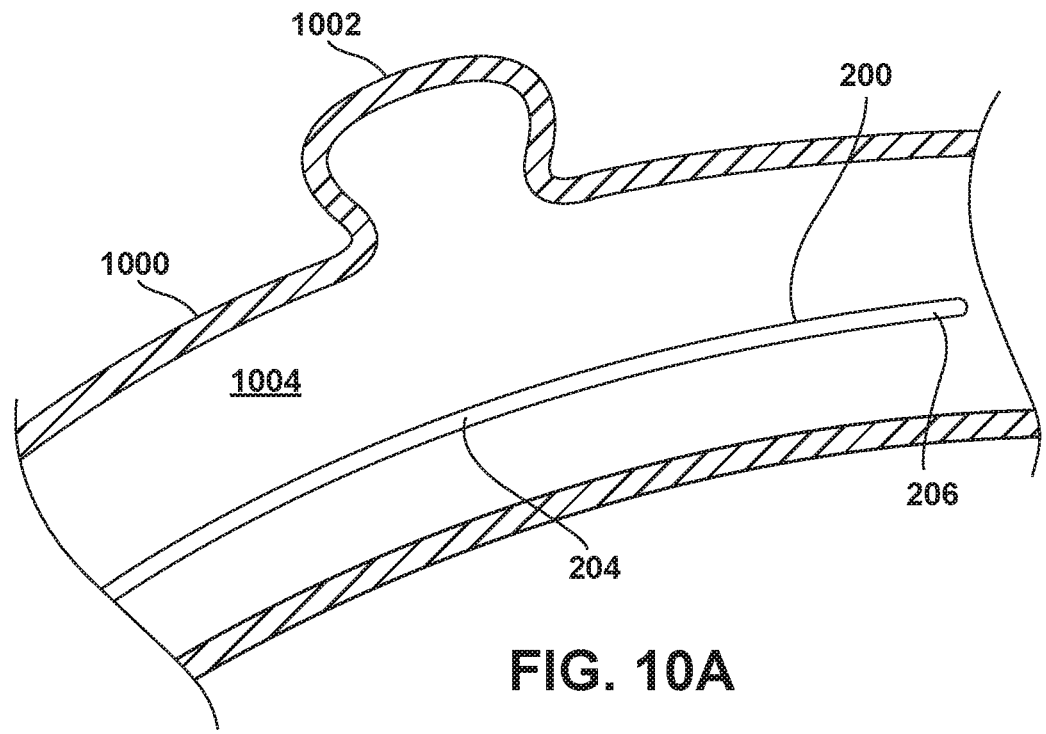
FIGS. 10A-10G are partial, schematic views of the system of FIG. 1 in various stages of use at an example treatment site within the vasculature of a patient.

Elongate body 204 of guidewire 200 may be inserted into vasculature 1000 of a patient (FIG. 10A). Elongate body 204 may be advanced through vascular lumen 1004 of vasculature 1000 to position the leading end 206 of the elongate body 204 adjacent to target location 1002 or distal to a treatment site adjacent the target location 1002 as determined by the clinician.

Figure 10B:
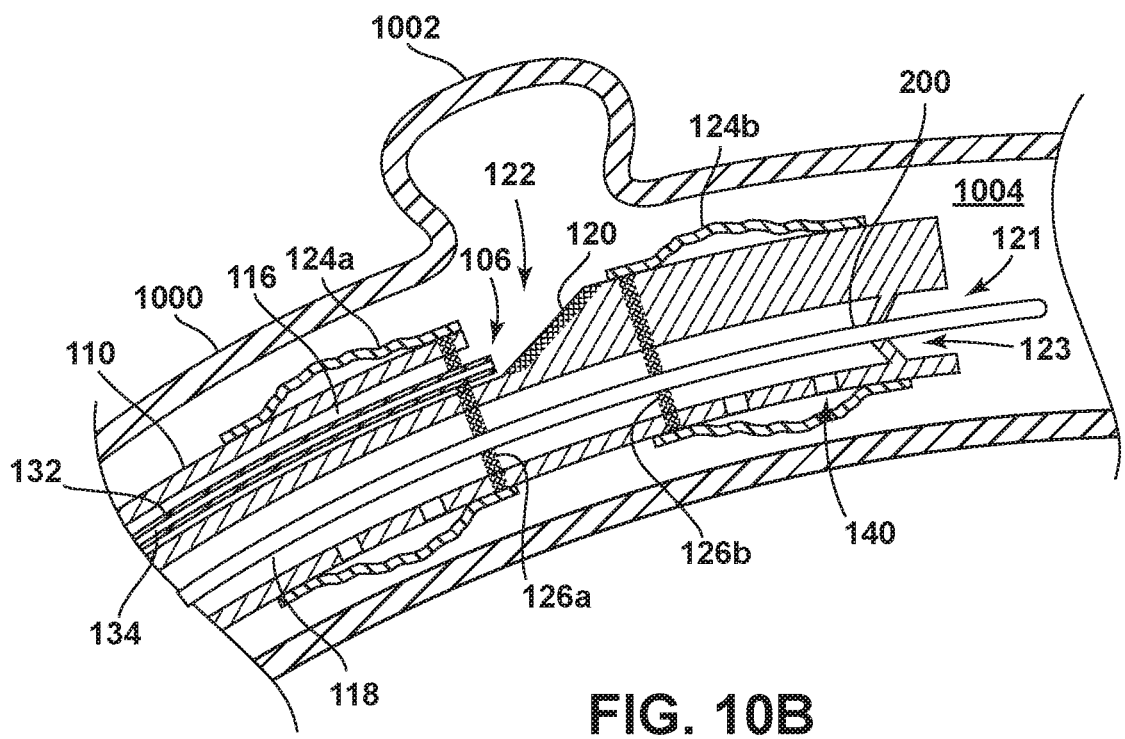
Figure 10C:
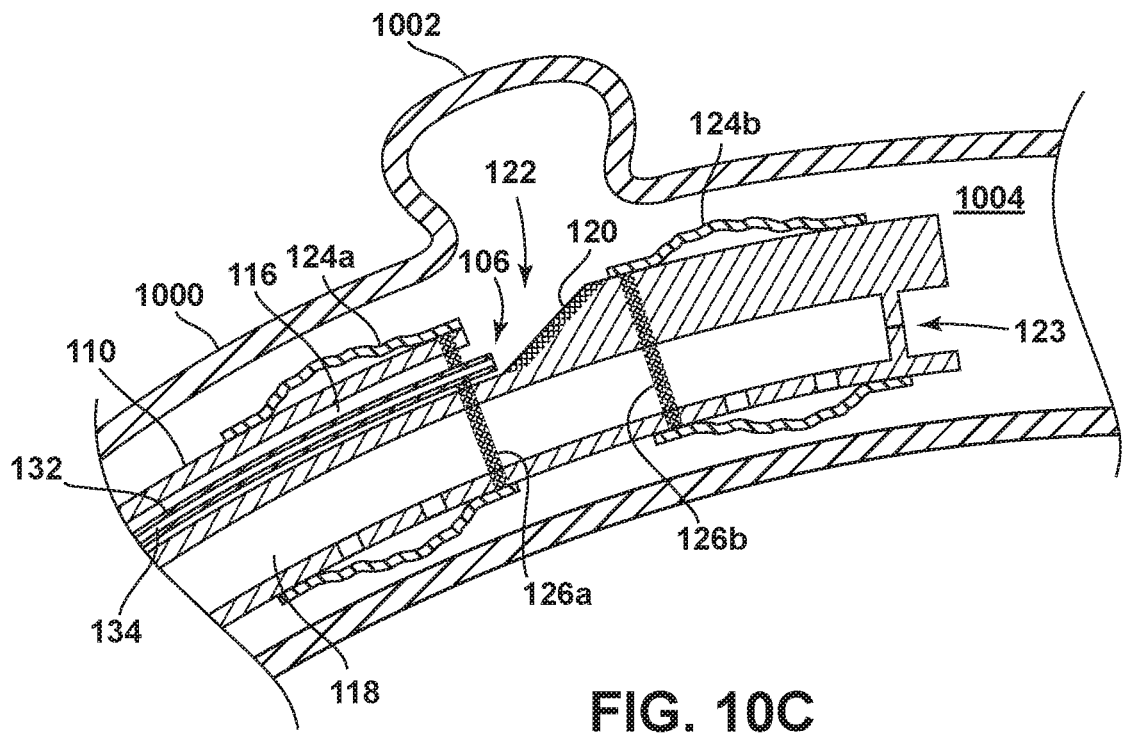

Outer catheter 102 may be introduced over elongate body 204 and a distal portion of outer catheter 102 may be advanced to a treatment site adjacent to target location 1002 (FIG. 10B). As the distal portion of outer catheter 102 is advanced over elongate body 204, valve 123 may establish a sealing relation with the elongate body 204 to help minimize or even prevent the influx of blood from vascular lumen 1004 into the second lumen 118 of catheter 102 through the distal access port 121. Radiopaque markers 126 and/or radiopaque material on surface 120, including, for example, a radiopaque polymer, may be used by the clinician to visualize the location of delivery port 122, surface 120, and/or expandable members 124 to position outer catheter 102 with respect to target location 1002. For example, radiopaque markers 126, located on either side of delivery port 122 and on inner ends of each of expandable members 124, may be helpful for positioning delivery port 122 adjacent to target location 1002 and/or to position expandable members 124 on either side of target location 1002. Alternatively or in addition, radiopaque material on surface 120 may be helpful for positioning surface 120 and delivery port 122 adjacent to target location 1002 and for rotationally orienting outer catheter 102 such that surface 120 forms a ramp leading toward target location 1002. A clinician may need to rotate catheter body 104 to orient surface 120 to form a ramp leading toward target location 1002.

Elongate body 204 may be retracted to remove elongate body 204 from second lumen 118 (FIG. 10C), while leaving outer catheter 102 in place. Valve 123 may substantially close second lumen 118 in the absence of the elongate body 204. Thus, the inflation holes 140 may be protected from an influx of blood or other fluids, which may otherwise clog the inflation holes 140.

Figure 10D:
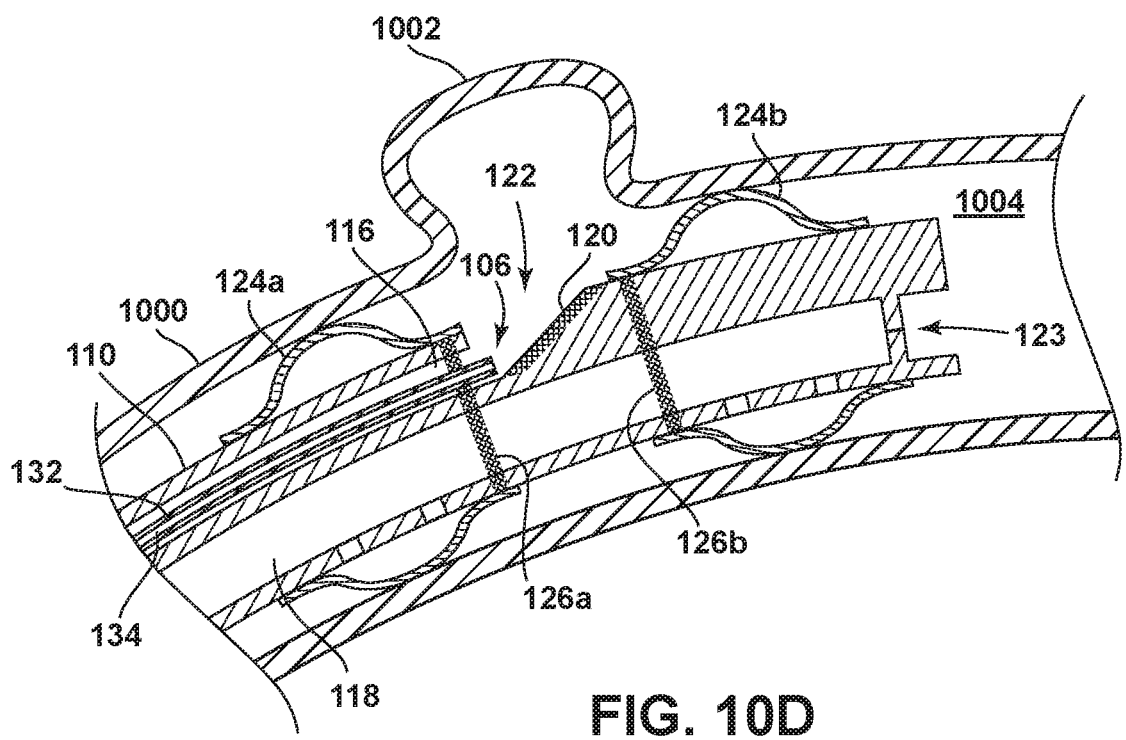

Prior to or after surface 120 and delivery port 122 are positioned adjacent to target location 1002, expandable members 124 may be inflated (FIG. 10D). For example, in some cases, expandable members 124 may be inflated to a state in which members 124 do not engage with the walls of vasculature 1000 enough to fix a position of catheter 102 relative to target location 1002, and then a clinician may manipulate the position of surface 120 and delivery port 122 prior to inflating expandable members 124 to engage with the walls of vasculature 1000 enough to fix the position of catheter 102. In other examples, however, expandable members 124 may not be inflated until surface 120 and delivery port 122 are positioned adjacent to target location 1002. Inflation fluid 137 (FIG. 1) may be introduced and transmitted through the second lumen 118 to inflate expandable members 124. Expandable members 124 may expand to engage interior wall portions of vasculature 1000 and may form a seal therewith to at least partially isolate target location 1002. Valve 123 (either alone, or in combination with the shaft of guidewire 200 when disposed in valve 123 when the members 124 are inflated with the guidewire so positioned) may help minimize or even prevent escape of the inflation fluid 137 through the distal access port 121 of second lumen 118.

Figure 10E:
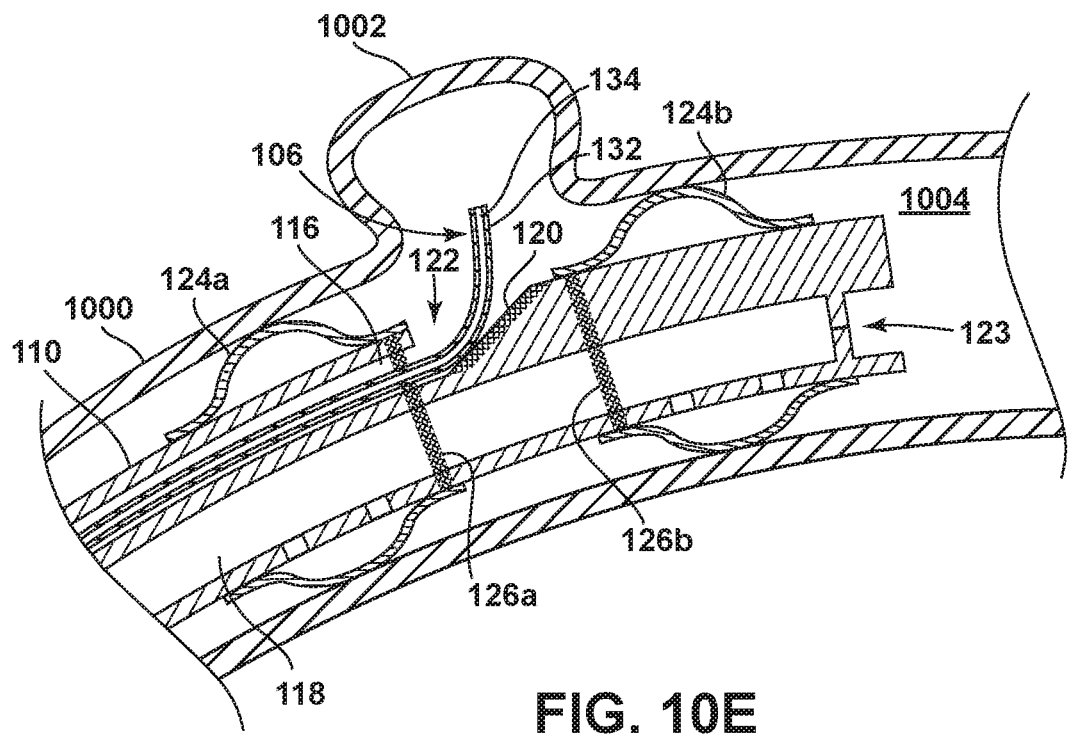

Inner catheter 106 may be advanced through first lumen 116 such that a distal portion of inner catheter 106 bends along surface 120 and advances past delivery port 122 (FIG. 10E).

Figure 10F:
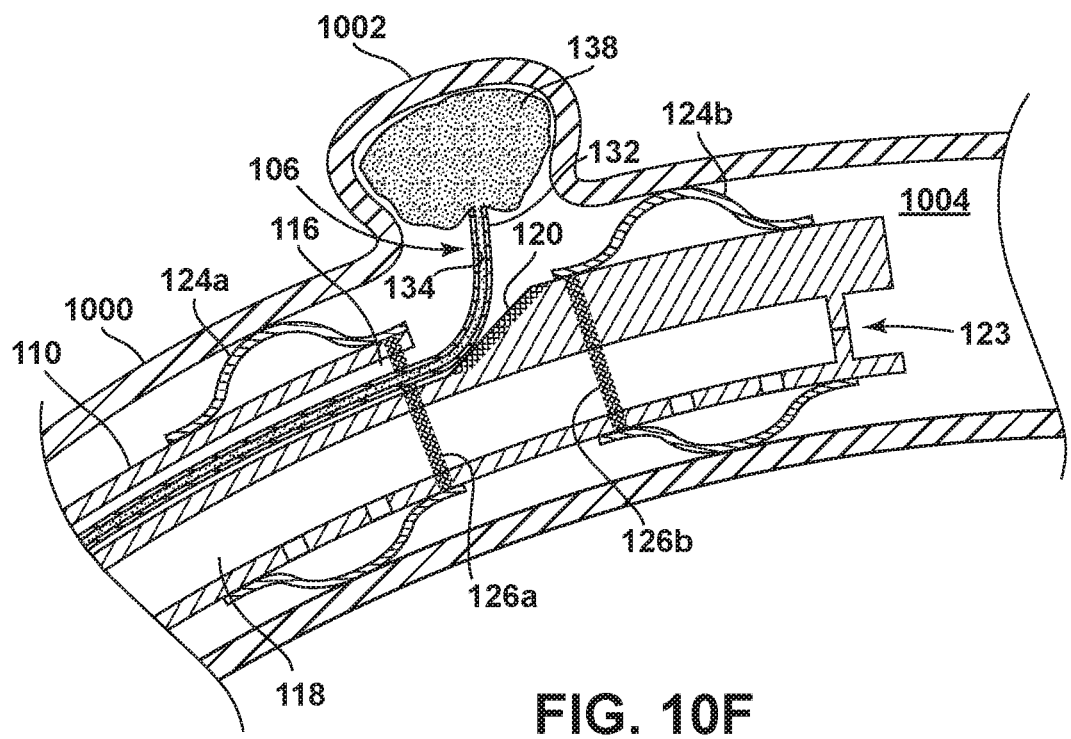

In the example shown in FIG. 10F, embolic composition 138 (and/or one or more coils, braids, implants, plugs, stents, or other devices or materials) may be delivered through inner catheter 106 to target location 1002. With expandable members 124 expanded, embolic composition 138 may be transmitted through first lumen 116 and expelled through the distal opening 136 of inner lumen 106. The flow of embolic composition 138 may be continued until the target location 1002 is filled to the desired level. During the procedure, backflow of the embolic composition 138 out of target location 1002 and into lumen 116 may be minimized or even prevented by the isolation of target location 1002 from blood flow by expandable members 124a and 124b. In some examples, first lumen 116 may include a valve formed within first lumen 116 or at delivery port 122 to form a seal around inner catheter 106 to help prevent backflow of the embolic composition 138 through first lumen 116 and/or to prevent influx of blood and/or other fluids into first lumen 116. In some examples, inner catheter 106 may substantially fill first lumen 116, thus preventing backflow of embolic composition 138 and/or influx of blood or other fluids through first lumen 116.

Figure 10G:
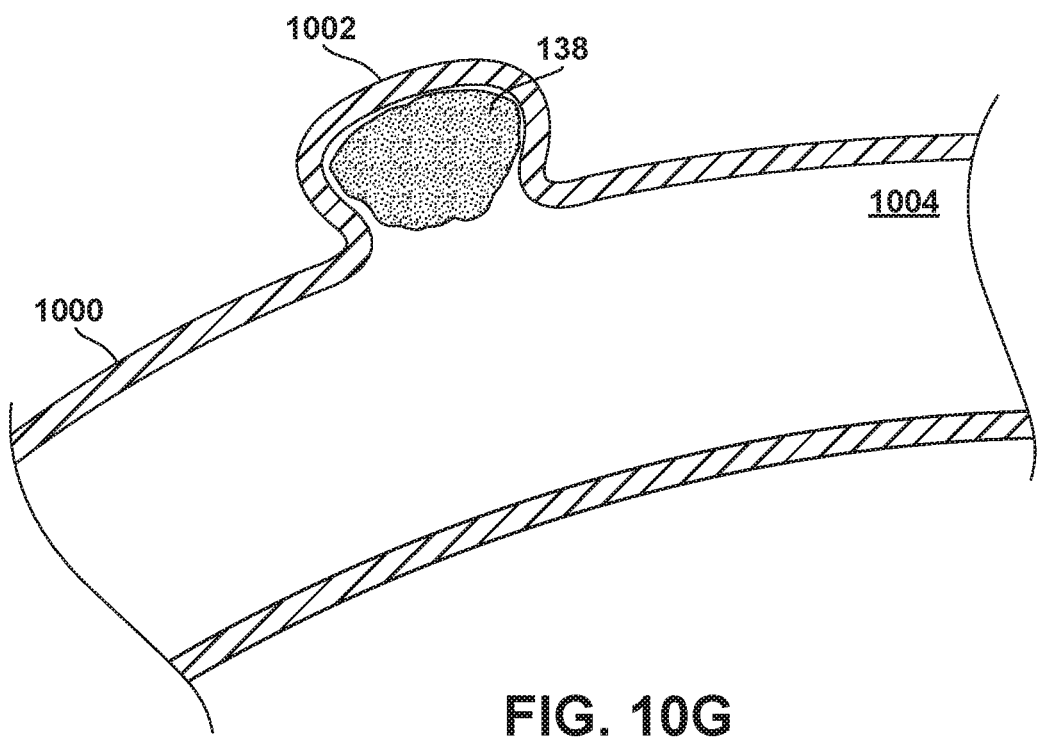

After the procedure is complete, system 10 may be removed from vasculature 1000 (FIG. 10G). For example, after embolic composition 138 solidifies within target location 1002, expandable members 124a and 124b may be deflated and distal portions of outer catheter 102 and inner catheter 106 withdrawn from vasculature 1000.

Although an example of use of system 10 has been described, any suitable modification may be made according to particular needs, including performing the steps in a different order and/or performing more, fewer steps, and/or different steps. For example, although inner catheter 106 has been described as delivering embolization fluid 138, inner catheter 106 and/or any suitable device received by outer catheter 102, may be used to deliver any suitable therapeutic agent and/or device. In some examples, inner catheter 106 may include additional components for securing and releasing an implantable medical device. In some examples, first lumen 116 may be configured to receive, in addition to or alternatively to inner catheter 106, another device for delivering a therapeutic agent and/or device to a target location. For example, first lumen 116 may be configured to receive a tethering device for delivering an embolic coil to target location 102. In some embodiments, first lumen 116 may be in fluid communication with a source of embolization fluid 138 and/or another therapeutic agent such that the embolization fluid 138 and/or therapeutic agent may be delivered through first lumen 116 and delivery port 122 without the use of inner catheter 106.

Additionally, although inner catheter 106 is shown as being disposed within first lumen 116 when outer catheter 102 is advanced along the elongate guidewire member 204 to a treatment site adjacent the target location 1002, inner catheter 106 may be introduced into first lumen 116 after outer catheter 102 is positioned. After delivery of embolization fluid 138 and/or another therapeutic agent or device by inner catheter 106, a distal end of inner catheter 106 may be retracted into first lumen 116 and/or inner catheter 106 may be retracted out of outer catheter 102 before retraction of outer catheter 102 from vasculature 1000 in order to avoid unwanted release of embolization fluid 138 into vasculature 1000 during retraction of outer catheter 102. For example, in some examples, inner catheter 106 may be retracted proximal to a valve within first lumen 116 or at delivery port 122. Vasculature 1000 may comprise, for example, the neurovasculature, peripheral vasculature, or cardiovasculature. Although a method of use is described from embolization of an aneurysm, catheter system 10 may be used for delivery of a therapeutic agent and/or device at any suitable location and for any suitable condition according to particular needs. Additionally, catheter system 10 may be used for delivery or an agent or device to any suitable type or aneurysm including, for example, a fusiform aneurysm.

Various examples have been described. These and other examples are within the scope of the following claims.

What is claimed is:

1. A catheter comprising:
a catheter body defining:
a catheter body outer surface;
a first lumen defining a first central longitudinal axis;
a second lumen defining a second central longitudinal axis spaced from the first central longitudinal axis in a direction orthogonal to the second central longitudinal axis;
a delivery port in fluid communication with the first lumen; and
a surface extending from the delivery port into the first lumen, wherein a junction between the surface and the catheter body outer surface defines an obtuse angle;
a first expandable member coupled to the catheter body proximal to the delivery port and in fluid communication with the second lumen;
a second expandable member coupled to the catheter body distal to the delivery port and in fluid communication with the second lumen, and
a valve configured to allow distal passage of a guidewire through the valve and through the second lumen, the valve being configured to prevent distal passage of a fluid through the valve and out of the second lumen.

2. The catheter of claim 1, wherein the first and second central longitudinal axes are substantially parallel.

3. The catheter of claim 1, wherein the catheter body defines a distal opening, the second lumen terminating at the distal opening.

4. The catheter of claim 1, wherein the second lumen extends distal to the first lumen.

5. The catheter of claim 1, wherein the first lumen terminates at the surface.

6. The catheter of claim 1, wherein the first lumen has a first cross-sectional area, and the second lumen has a second cross-sectional area, the cross-sections being taken in a direction substantially orthogonal to one of the first or second central longitudinal axes, and the first and second cross-sectional areas being substantially equal.

7. The catheter of claim 1, wherein the first lumen has a first cross-sectional area, and the second lumen has a second cross-sectional area, the cross-sections being taken in a direction substantially orthogonal to one of the first or second central longitudinal axes, and the first and second cross-sectional areas being different.

8. The catheter of claim 1, wherein the first expandable member comprises a first inflatable balloon, and the second expandable member comprises a second inflatable balloon.

9. The catheter of claim 1, wherein the surface comprises a radiopaque material.

10. The catheter of claim 1, wherein:
the first expandable member, when expanded, defines a first dimension measured in a direction substantially orthogonal to the second central longitudinal axis,
the second expandable member, when expanded, defines a second dimension measured in the direction substantially orthogonal to the second central longitudinal,
the first and second dimensions being different.

11. The catheter of claim 1, wherein:
the first expandable member, when expanded, defines a first dimension measured in a direction substantially orthogonal to the second central longitudinal axis, the second expandable member, when expanded, defines a second dimension measured in the direction substantially orthogonal to the second central longitudinal, the first and second dimensions being substantially equal.

12. The catheter of claim 1, wherein the first expandable member has a different compliancy than the second expandable member.

13. The catheter of claim 1, wherein a distal end of the first expandable member is longitudinally spaced from a proximal end of the second expandable member by about 10 millimeters to about 50 millimeters.

14. The catheter of claim 1, further comprising at least one radiopaque marker adjacent to the delivery port.

15. The catheter of claim 1, further comprising:
a first radiopaque marker proximal to the delivery port; and
a second radiopaque marker distal to the delivery port.

16. A system comprising:
a first catheter comprising:
a catheter body defining:
a catheter body outer surface;
a first lumen defining a first central longitudinal axis;
a second lumen defining a second central longitudinal axis spaced from the first central longitudinal axis in a direction orthogonal to the second central longitudinal axis;
a delivery port in fluid communication with the first lumen; and
a surface extending from the delivery port into the first lumen, wherein a junction between the surface and the catheter body outer surface defines an obtuse angle;
a first expandable member coupled to the catheter body proximal to the delivery port and in fluid communication with the second lumen;
a second expandable member coupled to the catheter body distal to the delivery port and in fluid communication with the second lumen; and
a valve configured to allow distal passage of a guidewire through the valve and through the second lumen, the valve being configured to prevent distal passage of a fluid through the valve and out of the second lumen; and
a second catheter configured to be received within the first lumen, wherein the surface is configured to guide a distal portion of the second catheter from the first lumen through the delivery por.

17. The system of claim 16, wherein the catheter body defines a distal opening, the second lumen terminating at the distal opening.

18. The system of claim 16, wherein the second lumen extends distal to the first lumen.

19. The catheter of claim 16, wherein the first lumen terminates at the surface.

20. The system of claim 16, further comprising the guidewire, wherein the second lumen is configured to receive the guidewire.

21. The system of claim 16, wherein the catheter body comprises a septum separating the first and second lumens, wherein the surface extends from the delivery port to the septum, the septum and the surface defining an obtuse angle.

22. The system of claim 16, wherein the catheter body comprises a first exterior wall and an interior wall defining the first lumen, and wherein the surface extends from a distal edge of the delivery port to the interior wall, the interior wall and the surface defining an obtuse angle.

23. The system of claim 16, wherein the surface comprises a radiopaque material.

24. The system of claim 16, wherein the catheter body comprises a distal member positioned distal to the first lumen, the distal member defining the surface.

25. A catheter comprising:
a catheter body defining:
a first lumen defining a first central longitudinal axis;
a second lumen defining a second central longitudinal axis spaced from the first central longitudinal axis in a direction orthogonal to the second central longitudinal axis;
a delivery port in fluid communication with the first lumen; and
a surface extending from the delivery port into the first lumen, wherein the surface is oriented at an obtuse or an acute angle relative to the first central longitudinal axis;
a first expandable member coupled to the catheter body proximal to the delivery port and in fluid communication with the second lumen;
a second expandable member coupled to the catheter body distal to the delivery port and in fluid communication with the second lumen; and
a valve configured to allow distal passage of a guidewire through the valve and through the second lumen, the valve being configured to prevent distal passage of a fluid through the valve and out of the second lumen.

* * * * *